US008854445B2

(12) United States Patent
Yamazaki

(10) Patent No.: US 8,854,445 B2
(45) Date of Patent: Oct. 7, 2014

(54) ENDOSCOPE APPARATUS

(75) Inventor: Kenji Yamazaki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 96 days.

(21) Appl. No.: 13/299,863

(22) Filed: Nov. 18, 2011

(65) Prior Publication Data

US 2012/0127292 A1    May 24, 2012

Related U.S. Application Data

(63) Continuation of application No. PCT/JP2011/063064, filed on Jun. 7, 2011.

(30) Foreign Application Priority Data

Jun. 28, 2010    (JP) .................................. 2010-146537

(51) Int. Cl.
| | | |
|---|---|---|
| H04N 7/18 | (2006.01) | |
| A61B 1/06 | (2006.01) | |
| A61B 1/00 | (2006.01) | |
| A61B 1/04 | (2006.01) | |
| A61B 1/05 | (2006.01) | |

(52) U.S. Cl.
CPC ........... *A61B 1/00009* (2013.01); *A61B 1/0646* (2013.01); *A61B 1/00059* (2013.01); *A61B 1/00186* (2013.01); *A61B 1/043* (2013.01); *A61B 1/0638* (2013.01); *A61B 1/051* (2013.01); *A61B 1/0669* (2013.01)
USPC ................... 348/71; 348/76; 348/68; 348/70; 348/65; 600/109; 600/160; 600/112; 600/178; 600/181; 600/101

(58) Field of Classification Search
None
See application file for complete search history.

(56) References Cited

U.S. PATENT DOCUMENTS

| | | | | |
|---|---|---|---|---|
| 4,885,633 A | * | 12/1989 | Buck | 348/135 |
| 7,860,180 B2 | * | 12/2010 | Reznic et al. | 375/261 |
| 2007/0153542 A1 | * | 7/2007 | Gono et al. | 362/574 |
| 2009/0066787 A1 | * | 3/2009 | Yamazaki | 348/70 |

FOREIGN PATENT DOCUMENTS

| | | |
|---|---|---|
| CN | 101010029 A | 8/2007 |
| CN | 101822525 A | 9/2010 |
| EP | 1 787 577 A1 | 5/2007 |
| EP | 2 016 884 A1 | 1/2009 |
| JP | 02-271822 | 11/1990 |
| JP | 06-339458 | 12/1994 |

(Continued)

*Primary Examiner* — Joseph Ustaris
*Assistant Examiner* — Edemio Navas, Jr.
(74) *Attorney, Agent, or Firm* — Scully, Scott, Murphy & Presser, P.C.

(57) ABSTRACT

An endoscope apparatus includes an image pickup section equipped with a color separation section that picks up an image of returning light from a subject illuminated by an illumination section, an emphasis processing section that performs emphasis processing on sharpness of an image signal generated from the output signal of the image pickup section and a storage section that stores information for modifying processing contents of the emphasis processing, wherein the storage section stores information for setting image signals to be subjected to emphasis processing in first and second observation modes in which images are picked up under illumination of white light and narrow band light respectively to a luminance signal and a color difference signal, and the emphasis processing section performs emphasis processing on the luminance signal with a greater emphasis characteristic than the color difference signal over an entire frequency domain.

7 Claims, 11 Drawing Sheets

(56) References Cited

FOREIGN PATENT DOCUMENTS

| JP | 2006-061620 | 3/2006 |
|----|-------------|--------|
| JP | 2006-061621 | 3/2006 |
| JP | 2006-068321 | 3/2006 |
| JP | 2007-300972 | 11/2007 |
| JP | 2008-086605 | 4/2008 |
| WO | WO 2006/025334 A1 | 3/2006 |
| WO | WO 2007/129570 A1 | 11/2007 |

* cited by examiner

FIG.13

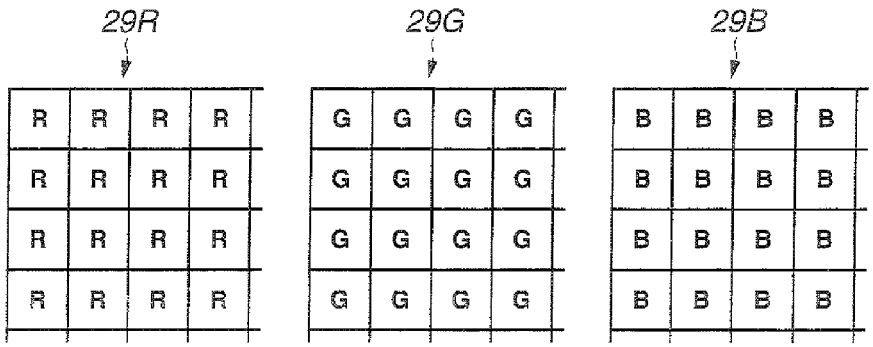

FIG.14

| IMAGE PICKUP SECTION | EMPHASIZED SIGNAL | AMOUNT OF EMPHASIS | REMARKS |
|---|---|---|---|
| COMPLEMENTARY COLOR SINGLE CCD | Y/Cr | Y > Cr | |
| PRIMARY COLOR SINGLE CCD/DOUBLE CCD | G/R | G > R | AFTER GR → YCr CONVERSION, AMOUNT OF EMPHASIS Y>Cr |
| PRIMARY COLOR TRIPLE CCD | G/R | G = R | AFTER GR → YCr CONVERSION, AMOUNT OF EMPHASIS Y = Cr |

FIG.15

| IMAGE PICKUP SECTION | EMPHASIZED SIGNAL | AMOUNT OF EMPHASIS | REMARKS |
|---|---|---|---|
| COMPLEMENTARY COLOR SINGLE CCD | Y/Cr/Cb | Y > Cr, Cb | |
| PRIMARY COLOR SINGLE CCD/DOUBLE CCD/TRIPLE CCD | B/R | B = R | AFTER BGR → YCrCb CONVERSION, AMOUNT OF EMPHASIS Y > Cr, Cb |

FIG.16

| IMAGE PICKUP SECTION | EMPHASIZED SIGNAL | AMOUNT OF EMPHASIS | REMARKS |
|---|---|---|---|
| COMPLEMENTARY COLOR SINGLE CCD | Y | – | |
| PRIMARY COLOR SINGLE CCD/DOUBLE CCD/TRIPLE CCD | B | – | AFTER BGR → YCrCb CONVERSION, EMPHASIS OF Y ONLY |

FIG.17

| IMAGE PICKUP SECTION | EMPHASIZED SIGNAL | AMOUNT OF EMPHASIS | REMARKS |
|---|---|---|---|
| COMPLEMENTARY COLOR SINGLE CCD | Y | – | |
| PRIMARY COLOR SINGLE CCD/DOUBLE CCD/TRIPLE CCD | R | – | AFTER BGR → YCrCb CONVERSION, EMPHASIS OF Y ONLY |

FIG. 18

| INCIDENT LIGHT | DE-EMPHASIZED (IMAGE) SIGNAL/SIGNAL FOR WHICH AMOUNT OF EMPHASIS IS REDUCED | | | | |
|---|---|---|---|---|---|
| | COLOR FILTER OF IMAGE PICKUP SECTION, NUMBER OF CCDS | | | | |
| | COMPLEMENTARY COLOR SINGLE CCD | PRIMARY COLOR SINGLE CCD | PRIMARY COLOR DOUBLE CCD | PRIMARY COLOR TRIPLE CCD | |
| WHITE COLOR | YCrCb/CrCb | | ↓ | BGR/NONE | |
| BLUE (INCLUDING NEAR-ULTRAVIOLET REGION) | YCb/Cb | | ↓ | BG/NONE | |
| GREEN | | | | | |
| GREEN TO RED (INCLUDING NEAR-INFRARED REGION) | YCr/Cr | | ↓ | GR/NONE | |
| BLUE (INCLUDING NEAR-ULTRAVIOLET REGION) | YCrCb/CrCb | | ↓ | BR/NONE | |
| RED (INCLUDING NEAR-INFRARED REGION) | | | | | |
| BLUE (INCLUDING NEAR-ULTRAVIOLET REGION) | Y/NONE | | ↓ | B/NONE | |
| RED (INCLUDING NEAR-INFRARED REGION) | Y/NONE | | ↓ | R/NONE | |

ENDOSCOPE APPARATUS

CROSS REFERENCE TO RELATED APPLICATION

This application is a continuation application of PCT/JP2011/063064 filed on Jun. 7, 2011 and claims benefit of Japanese Application No. 2010-146537 filed in Japan on Jun. 28, 2010, the entire contents of which are incorporated herein by this reference.

BACKGROUND OF THE INVENTION

1. Field of the Invention

The present invention relates to an endoscope apparatus that performs image processing on image pickup means mounted on an endoscope.

2. Description of the Related Art

In recent years, electronic endoscopes equipped with image pickup means have been widely used in various endoscope inspections or the like.

When an endoscope inspection is performed, such endoscope apparatuses are available as a simultaneous endoscope apparatus that picks up a color image using an electronic endoscope equipped with an image pickup device provided with a color filter under illumination of white light and a frame sequential endoscope apparatus that picks up an image under frame sequential illuminating light of R, G and B using an electronic endoscope equipped with a monochrome image pickup device, and these endoscope apparatuses have different signal processing systems (image processing systems).

As a first conventional example of the endoscope apparatus using an electronic endoscope equipped with an image pickup device provided with a color filter, Japanese Patent Publication No. 4009626 discloses an endoscope apparatus equipped with an emphasis circuit that emphasizes contours or a structure for only luminance signals.

On the other hand, as a second conventional example of the endoscope apparatus using an electronic endoscope equipped with an image pickup device provided with a color filter, Japanese Patent Application Laid-Open Publication No. 2006-61621 discloses an endoscope apparatus that performs emphasis processing on luminance signals and color difference signals.

SUMMARY OF THE INVENTION

An endoscope apparatus according to an aspect of the present invention includes an image pickup section equipped with a color separation section that color-separates and receives returning light of light radiated onto a subject by an illumination section to pick up an image of the subject, an emphasis processing section that performs emphasis processing on sharpness of an image signal based on the image pickup section, a storage section that stores information for modifying processing contents of the emphasis processing section according to spectral characteristics of the returning light incident on the image pickup section which differ depending on a type of the image pickup section and an observation mode and a control section that performs control of modifying the processing contents of the emphasis processing section based on the information of the storage section, wherein the storage section sets, when the observation mode is a first observation mode in which image pickup is performed under illumination of white light, an image signal to be subjected to emphasis processing by the emphasis processing section to a luminance signal and two color difference signals, and stores, when the observation mode is a second observation mode in which image pickup is performed under illumination of narrow band illuminating light, information for setting an image signal to be subjected to emphasis processing by the emphasis processing section to a luminance signal and one color difference signal, and in the first observation mode and the second observation mode, the emphasis processing section performs emphasis processing on the luminance signal in the image signal with a greater emphasis characteristic than the color difference signal in the image signal over an entire frequency domain.

An endoscope apparatus according to another aspect of the present invention includes an image pickup section equipped with a color separation section that color-separates and receives returning light of light radiated onto a subject by an illumination section to pick up an image of the subject, an emphasis processing section that performs emphasis processing on sharpness of an image signal based on the image pickup section, a storage section that stores information for modifying processing contents of the emphasis processing section according to spectral characteristics of the returning light incident on the image pickup section which differ depending on a type of the image pickup section and an observation mode and a control section that performs control of modifying the processing contents of the emphasis processing section based on the information of the storage section, wherein the storage section sets, when the observation mode is a first observation mode in which image pickup is performed under illumination of white light, an image signal to be subjected to emphasis processing by the emphasis processing section to a luminance signal and two color difference signals, and stores, when the observation mode is a second observation mode in which image pickup is performed under illumination of narrow band illuminating light, information for setting an image signal to be subjected to emphasis processing by the emphasis processing section to a luminance signal and one color difference signal, and in the first observation mode and the second observation mode, the emphasis processing section performs emphasis processing on the color difference signal in the image signal with a smaller emphasis characteristic than the luminance signal in the image signal in a frequency domain on a high frequency side having a higher frequency.

An endoscope apparatus according to a further aspect of the present invention includes an image pickup section equipped with a color separation section that color-separates and receives returning light of light radiated onto a subject by an illumination section to pick up an image of the subject, an emphasis processing section that performs emphasis processing on sharpness of an image signal based on the image pickup section, a storage section that stores information for modifying processing contents of the emphasis processing section according to spectral characteristics of the returning light incident on the image pickup section which differ depending on a type of the image pickup section and an observation mode and a control section that performs control of modifying the processing contents of the emphasis processing section based on the information of the storage section, wherein the storage section stores information for setting an image signal to be subjected to emphasis processing by the emphasis processing section to color signals of R, G and B according to an array structure corresponding to unit pixels of a plurality of filter elements having different transmission characteristics and making up the color separation section when the observation mode is a first observation mode in which image pickup is performed under illumination of white light and setting the image signal so as to emphasize the color signal of G more than the color signal of B to be subjected to emphasis processing by the emphasis processing section when the observation mode is a second observation mode in which image pickup is performed under illumination of narrow band illuminating light.

BRIEF DESCRIPTION OF THE DRAWINGS

FIG. 13 is a diagram illustrating color separation into three primary colors by a triple CCD image pickup section;

FIG. 14 is a diagram illustrating an example of setting emphasis characteristics with respect to an emphasized signal emphasized by the emphasis circuit depending on whether the image pickup section adopts a complementary color single CCD, primary color single CCD, double CCD or primary color triple CCD when applied to a fluorescent mode according to a fourth embodiment of the present invention;

FIG. 15 is a diagram illustrating an example of setting emphasis characteristics with respect to an emphasized signal emphasized by the emphasis circuit depending on whether the image pickup section adopts a complementary color single CCD, primary color single CCD, double CCD or triple CCD when images of fluorescent blue color and red color light are picked up to generate an observed image;

FIG. 16 is a diagram illustrating an example of setting emphasis characteristics with respect to an emphasized signal emphasized by the emphasis circuit depending on whether the image pickup section adopts a complementary color single CCD, primary color single CCD, double CCD or triple CCD when an image of blue color light is picked up to generate an observed image;

FIG. 17 is a diagram illustrating an example of setting emphasis characteristics with respect to an emphasized signal emphasized by the emphasis circuit depending on whether the image pickup section adopts a complementary color single CCD, primary color single CCD, double CCD or triple CCD when an image of red color light is picked up to generate an observed image; and FIG. 18 is a diagram illustrating an overview of incident light, an emphasized signal emphasized by the emphasis circuit and a signal whose amount of emphasis is reduced according to the present invention.

DETAILED DESCRIPTION OF THE PREFERRED EMBODIMENTS

Hereinafter, embodiments of the present invention will be described with reference to the accompanying drawings.

First Embodiment

Figure 1:
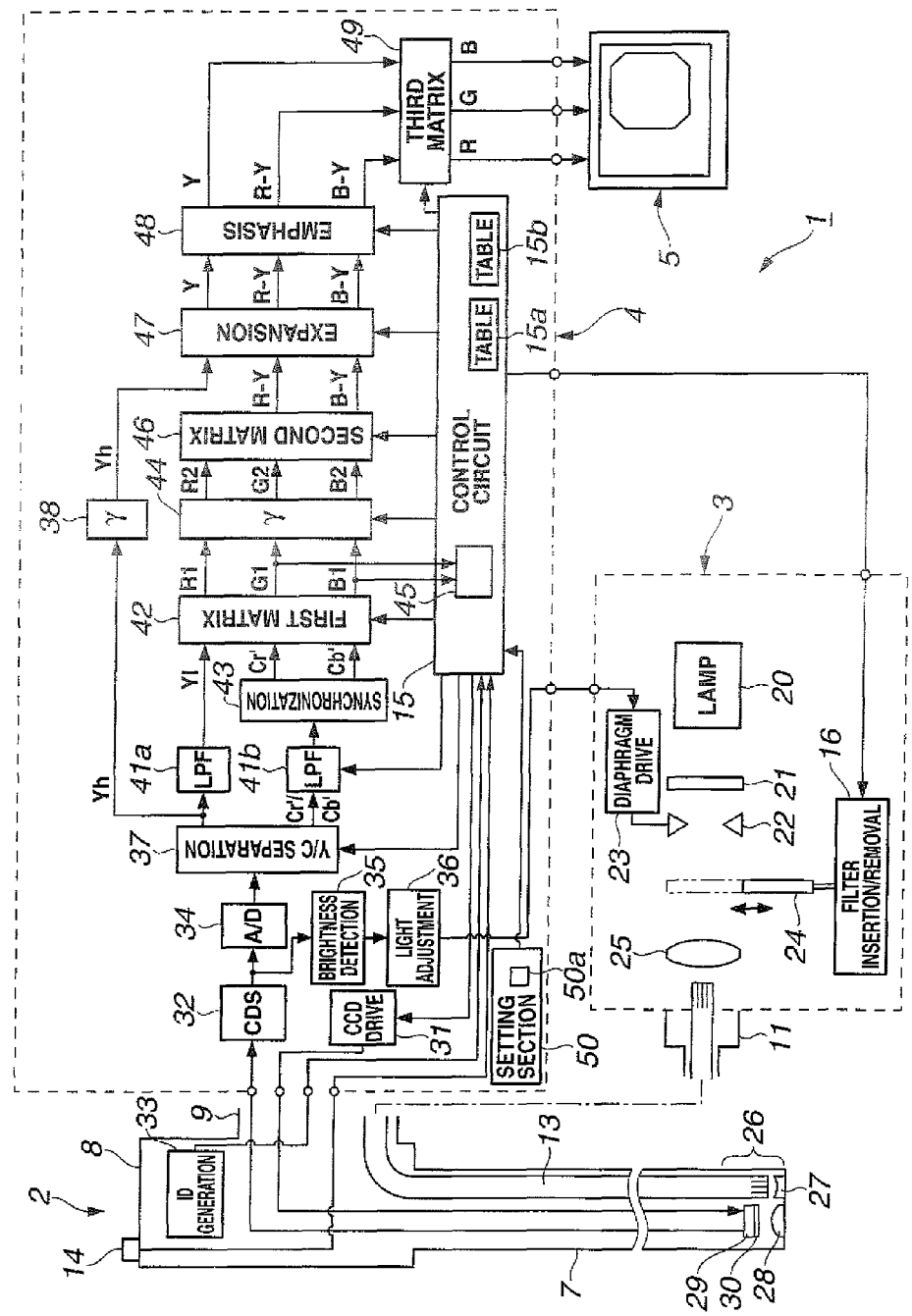
FIG. 1 is a block diagram illustrating a configuration of an endoscope apparatus according to a first embodiment of the present invention.

As shown in FIG. 1, an endoscope apparatus 1 according to a first embodiment is provided with an electronic endoscope (hereinafter, simply abbreviated to "endoscope") 2 inserted into a body cavity for performing an endoscope inspection and a light source device 3 that supplies illuminating light to the endoscope 2. Furthermore, the endoscope apparatus 1 is also provided with a video processor 4 as an endoscope video signal processing apparatus that drives image pickup means incorporated in the endoscope 2 and performs signal processing on an output signal of the image pickup means and a monitor 5 that displays an image obtained by applying signal processing to the pickup image captured by the image pickup means by receiving the video signal outputted from the video processor 4 as an endoscope image.

The endoscope 2 includes an elongated insertion portion 7, an operation section 8 provided at a rear end of the insertion portion 7 and a universal cable 9 that extends from the operation section 8, and a light guide connector 11 at an end of the universal cable 9 is detachably connected to the light source device 3, and a signal connector is detachably connected to the video processor 4.

A light guide 13 for transmitting illuminating light is inserted into the insertion portion 7 and illuminating light from the light source device 3 is supplied to the light guide 13 by connecting the light guide connector 11 at an end of the operator's hand side in the light guide 13 to the light source device 3.

The light source device 3 generates white illuminating light to cover a visible wavelength region as illuminating light and supplies the white illuminating light to the light guide 13 in normal white light imaging (abbreviated to "WLI") mode.

On the other hand, in narrow band imaging (abbreviated to "NBI") mode, the light source device 3 generates narrow band illuminating light as illuminating light and supplies it to the light guide 13.

Changeover between the WLI mode and NBI mode can be instructed using, for example, a mode changeover switch 14 made up of a scope switch provided in the operation section 8 of the endoscope 2. The mode changeover switch 14 may be made up of not only the scope switch provided in the endoscope 2 but also a foot switch, or the mode changeover switch may be provided on the front panel of the video processor 4 or may be made up of a keyboard (not shown).

A changeover signal from the mode changeover switch 14 is inputted to a control circuit 15 in the video processor 4 and when the changeover signal is inputted, the control circuit 15 controls a filter insertion/removal mechanism 16 of the light source device 3 to selectively switch between normal white light and narrow band illuminating light.

Furthermore, as will be described later, this control circuit 15 also performs control of changing characteristics of the signal processing system in the video processor 4 operating in conjunction with the changeover control of illuminating light supplied from the light source device 3 to the light guide 13. Signal processing suitable for respective observation modes of the WLI mode and NBI mode can be performed by changing characteristics of the signal processing system through a changeover operation using the mode changeover switch 14.

The light source device 3 incorporates a lamp 20 that generates illuminating light and the lamp 20 generates illuminating light including a visible wavelength region. With infrared light thereof cut by an infrared cut filter 21, the illuminating light is converted to illuminating light of a wavelength close to a wavelength band of quasi-white light and then impinged on a diaphragm 22. The aperture of the diaphragm 22 is adjusted by a diaphragm drive circuit 23 and the quantity of light passing therethrough is thereby controlled.

The illuminating light that passes through the diaphragm 22 is condensed by a condensing lens 25 after passing through a narrow band filter 24 which is inserted/removed into/from an illuminating light path by the filter insertion/removal mechanism 16 made up of a plunger or the like in the NBI mode or without passing through the narrow band filter 24 in the WLI mode, and made to impinge on an end face on the operator's hand side of the light guide 13, that is, on the incident end face.

Figure 2:
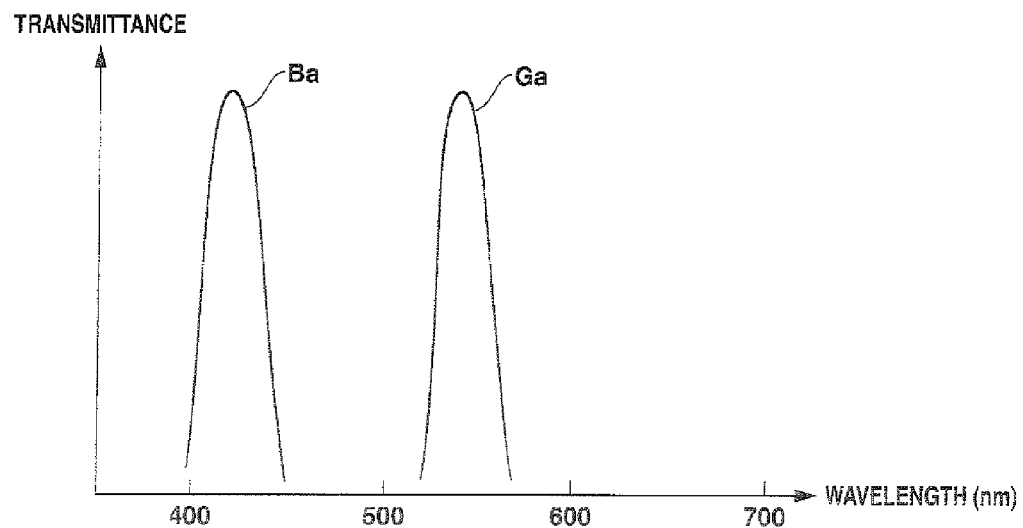
FIG. 2 is a characteristic diagram illustrating an example of spectral characteristics of a narrow band filter.

FIG. 2 shows an example of spectral characteristics of the narrow band filter 24. The narrow band filter 24 shows a two-peak filter characteristic and has, for example, narrow band pass filter characteristic parts Ga and Ba in wavelength regions of green (G) and blue (B) respectively.

To be more specific, the narrow band pass filter characteristic parts Ga and Ba have center wave lengths of 540 nm and 420 nm respectively and band pass characteristics having a full width at half maximum of 20 to 40 nm.

Therefore, when the narrow band filter 24 is placed in the illuminating light path, two bands of narrow band illuminating light that have passed through the narrow band pass filter characteristic parts Ga and Ba are made to impinge on the light guide 13.

On the other hand, when the narrow band filter 24 is not placed in the illuminating light path, wide band white light is supplied to the light guide 13.

The illuminating light from the light guide 13 is transmitted to the distal end face thereof through the light guide 13, outputted via an illumination lens 27 making up illumination means attached to an illuminating window provided at a distal end portion 26 of the insertion portion 7 and radiated onto, for example, the surface of a living tissue such as a diseased part in the body cavity as a subject to irradiate the surface with illuminating light.

An observation window is provided adjacent to the illuminating window at the distal end portion 26 and an objective lens 28 is fitted into the observation window. This objective lens 28 forms an optical image from, for example, reflected light as returning light (or incident light) from the living tissue as a subject. One charge coupled device (abbreviated to "CCD") 29 as an image pickup device making up image pickup means is placed at the image forming position of the objective lens 28 and the optical image is photoelectrically converted by the CCD 29.

Figure 3:
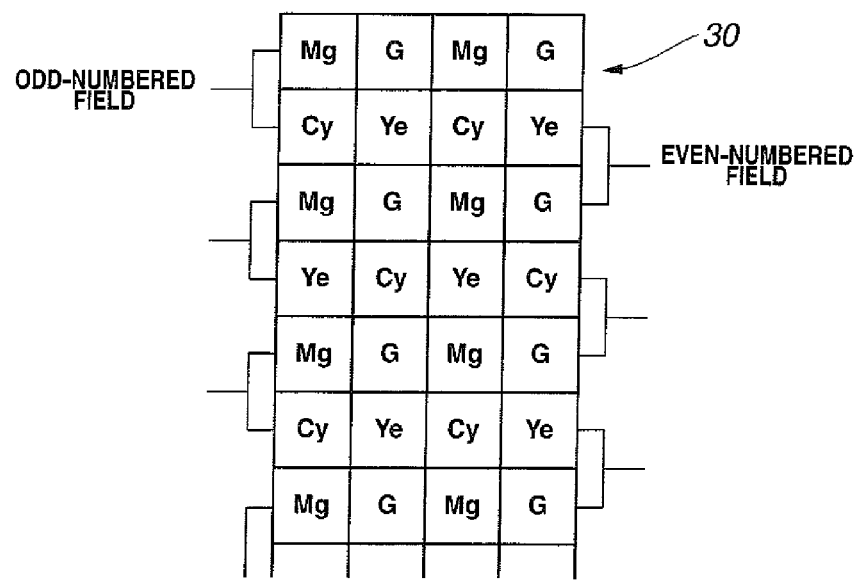
FIG. 3 is a diagram illustrating a configuration of a filter array of a color separation filter provided in a solid image pickup device.

For example, a complementary color filter as shown in FIG. 3 is mounted in pixel units on the image pickup surface of the CCD 29 as a color filter 30 having a function of a color separation section that performs optical color separation and color image pickup. That is, the image pickup section (image pickup device) of the present embodiment is an image pickup device with a complementary color single CCD.

In the complementary color filter, four color chips of magenta (Mg), green (G), cyan (Cy) and yellow (Ye) are arranged in front of each pixel, Mg and G are alternately arranged in the horizontal direction, and an array of Mg, Cy, Mg, Ye and an array of G, Ye, G, Cy are arranged sequentially in the vertical direction. In this two-dimensional array structure, two pixels in the horizontal direction and four pixels in the vertical direction, a total of eight periodically arrayed pixels constitute a (two-dimensional) array structure which is a unit of performing color image pickup.

The CCD 29 using the complementary color filter adds up and sequentially reads two columns of pixels neighboring each other in the vertical direction, and reads pixels by shifting the column of pixels between an odd-numbered field and an even-numbered field. From the signal read from the CCD 29, a Y/C separation circuit 37 (as first color separation means) located after the CCD 29 generates a luminance signal and a color difference signal, as is publicly known.

An emphasis characteristic is set by an emphasis circuit 48, which will be described later, according to the unit array structure of the color filter 30 in FIG. 3, that is, pixel density per color signal.

The above-described CCD 29 is connected to one end of the signal line and by connecting a signal connector to which the other end of the signal line is connected to the video processor 4, the CCD 29 is connected to a CCD drive circuit 31 and a CDS circuit 32 in the video processor 4.

Each endoscope 2 is provided with an ID generation section 33 that generates identification information (ID) specific to the endoscope 2, the ID from the ID generation section 33 is inputted to the control circuit 15 and the control circuit 15 identifies the type of the endoscope 2 connected to the video processor 4, the number and types or the like of pixels of the CCD 29 incorporated in the endoscope 2 using the ID.

The control circuit 15 then controls the CCD drive circuit 31 so as to appropriately drive the CCD 29 of identified endoscope 2.

In the CCD 29, the image pickup signal photoelectrically converted with application of the CCD drive signal from the CCD drive circuit 31 is inputted to the correlation double sampling circuit (abbreviated to "CDS circuit") 32. A signal component is extracted by the CDS circuit 32 from an image pickup signal, converted to a baseband signal, then inputted to an A/D conversion circuit 34 to be converted to a digital signal, and then inputted to a brightness detection circuit 35 where brightness (average luminance of the signal) is detected.

The brightness signal detected by the brightness detection circuit 35 is inputted to a light adjustment circuit 36 and a light adjustment signal for adjusting light based on a difference from a reference brightness (light adjustment target value) is generated. The light adjustment signal from this light adjustment circuit 36 is inputted to the diaphragm drive circuit 23 and the diaphragm drive circuit 23 adjusts the aperture of the diaphragm 22 so as to obtain the reference brightness.

The digital signal outputted from the A/D conversion circuit 34 is inputted to the Y/C separation circuit 37 and the Y/C separation circuit 37 generates a luminance signal Y and line sequential color difference signals Cr' and Cb' (as a color signal C in a broad sense). The Y/C separation circuit 37 forms first color separation means.

The luminance signal Y is inputted to an expansion circuit 47 via a γ circuit 38 (this luminance signal is represented by Yh) and also inputted to a first low pass filter (abbreviated to "LPF") 41a which limits the passband of the signal.

The LPF 41a is set to a wide passband in correspondence with the luminance signal Y and a luminance signal Y1 of a band set by the passband characteristic of this LPF 41*a* is inputted to a first matrix circuit 42.

Furthermore, the color difference signals Cr' and Cb' are inputted to a (line sequential) synchronization circuit 43 via a second LPF 41*b* that limits the passband of the signal.

In this case, the passband characteristic of the second LPF 41*b* is modified by the control circuit 15 according to the observation mode. To be more specific, in the WLI mode, the second LPF 41*b* is set to a lower band than the first LPF 41*a*. That is, in the WLI mode, a setting is made so as to perform signal processing (image processing) in conformity with a typical video signal standard.

On the other hand, in the NBI mode, the second LPF 41*b* is modified to a wider band than the low band in the WLI mode. For example, the second LPF 41*b* is set (modified) to a wide band in substantially the same way as the first LPF 41*a*.

Thus, the second LPF 41*b* forms processing characteristic modifying means for modifying the processing characteristic of limiting the passband of the color difference signals Cr' and Cb' in conjunction with changeover of the observation mode.

By widening the signal passband characteristic of the second LPF 41*b*, it is possible to improve the resolution of the running state of a capillary vessel or the running state of blood vessel close to the surface layer obtained by a color signal of G, an image of which is picked up under illuminating light of G close to the luminance signal from the narrow band pass filter characteristic part Ga and obtain an image of high image quality, easy to diagnose.

The synchronization circuit 43 generates synchronized color difference signals Cr' and Cb', and the color difference signals Cr' and Cb' are inputted to the first matrix circuit 42.

The first matrix circuit 42 converts the luminance signal Y1 and the color difference signals Cr' and Cb' to three primary color signals R1, G1 and B1. The first matrix circuit 42 outputs the three primary color signals R1, G1 and B1 generated to a γ circuit 44 that performs gamma correction. As described above, although no illuminating light of a red wavelength band is used in the NBI mode, the color signal R1 is equalized to the color signal G1 by a matrix Mat1 shown in [Equation 4] which will be described later.

The (two color signals G1 and B1 of) three primary color signals R1, G1 and B1 are also inputted, for example, to the control circuit 15 and a signal intensity ratio calculation circuit 45 in the control circuit 15 calculates a signal intensity ratio between the color signals G1 and B1 in the NBI mode. The signal intensity ratio calculation circuit 45 is not necessarily provided inside the control circuit 15, but a configuration may be adopted in which the signal intensity ratio calculation circuit 45 is provided outside the control circuit 15 and the calculated signal intensity ratio is outputted to the control circuit 15.

The signal intensity ratio calculation circuit 45 accumulates signal levels of the color signals G1 and B1 in field or frame units and calculates signal intensity ratios t and u of the color signals G1 and B1 based on the accumulation result.

The signal intensity ratio calculation circuit 45 may also calculate the signal intensity ratios t and u by accumulating signal levels within a predetermined region set within an image region, for example, of one field or one frame.

Assuming the accumulated values of the color signals G1 and B1 within the predetermined region are iG and iB respectively, the signal intensity ratios t and u are:

$$t=iG/(iG+iB), u=iB/(iG+iB) \quad (1)$$

This satisfies a condition of t+u=1. Therefore, the two signal intensity ratios t and u may be calculated or one of the two may be calculated and the remaining one may be calculated from the condition of t+u=1. The values of the signal intensity ratios t and u are reflected in matrix Mat3 for matrix calculation by a third matrix circuit 49 which will be described later.

Without being limited to the case of accumulating in field or frame units to dynamically calculate the signal intensity ratios t and u (that is, signal intensity ratios t and u dynamically change), the signal intensity ratios t and u may be calculated and values may be fixed to the calculated values at timing of an initial setting or timing instructed by a user such as an operator.

The first matrix circuit 42 is controlled by the control circuit 15 and converts the values of the matrix coefficients (that determine conversion characteristics by the first matrix circuit 42) to the modified three primary color signals R1, G1 and B1 according to the characteristics of the color filter 30 of the CCD 29 and the characteristics of the narrow band filter 24.

For example, the characteristics of the color filter 30 of the CCD 29 mounted in the endoscope 2 may vary depending on the endoscope 2 actually connected to the video processor 4 and the control circuit 15 changes matrix coefficients to be converted to the three primary color signals R1, G1 and B1 by the first matrix circuit 42 according to the type of the CCD 29 actually used and the spectral characteristics of the color filter 30 according to the ID information.

The control circuit 15 incorporates a reference table 15*a* to be looked up to set matrix coefficients by the first matrix circuit 42, the second matrix circuit 46 and the third matrix circuit 49, which will be described later.

The γ circuit 44 is also controlled by the control circuit 15. To be more specific, in the NBI mode, characteristics are modified to γ characteristics with γ correction characteristics more emphasized than in the WLI mode. As a result, the contrast on the low signal level side is emphasized and display characteristics easier to identify are obtained.

The three primary color signals R2, G2 and B2 γ-corrected by the γ circuit 44 are inputted to the second matrix circuit 46 and converted to color difference signals R-Y and B-Y by the second matrix circuit 46 as follows.

[Equation 1]

$$\begin{bmatrix} R \\ R-Y \\ B-Y \end{bmatrix} = Mat2 \cdot \begin{bmatrix} R2 \\ G2 \\ B2 \end{bmatrix}$$

Matrix Mat2 is expressed as shown in Equation (2b).

For example, matrix coefficients of fixed values (common set values) are adopted for the second matrix circuit 46 irrespective of whether the observation mode is changed to the WLI mode or NBI mode.

The color difference signals R-Y and B-Y outputted from the second matrix circuit 46, together with the luminance signal Yh gamma-corrected by the γ circuit 38, are inputted to the expansion circuit 47 that performs expansion processing.

The luminance signal Yh (hereinafter described as "Y" for simplicity) and the color difference signals R-Y and B-Y are subjected to expansion processing by the expansion circuit 47 and then inputted to the emphasis circuit 48 as emphasis processing means for performing sharpness emphasis processing. The expansion circuit 47 and the emphasis circuit 48 are provided in a 3-circuit configuration in correspondence with the luminance signal Y and the two color difference signals R-Y and B-Y.

The emphasis circuit 48 emphasizes the sharpness of contours or structure of a mucous membrane image reproduced to an image signal and outputs the emphasized luminance signal Y and color difference signals R-Y and B-Y to the third matrix circuit 49 as second color separation means.

The expansion processing by the expansion circuit 47 and the emphasis processing by the emphasis circuit 48 are controlled by the control circuit 15 as control means.

Furthermore, the control circuit 15 has a table 15b as storing means for storing the type (class) of the CCD 29 as image pickup means and information for modifying (changing) processing contents of the emphasis circuit 48 according to spectral characteristics of light (incident on the CCD 29) which vary depending on the observation mode.

The table 15b as the above-described storing means may also be provided outside the control circuit 15. Furthermore, the table 15b may also be provided inside the emphasis circuit 48.

The control circuit 15 forms control means for performing control of reading the type of the CCD 29 and the information corresponding to the observation mode from the table 15b and automatically modifying processing contents of the emphasis circuit 48 according to the information.

The control circuit 15 recognizes the type of the CCD 29 using the ID from the ID generation section 33. Furthermore, the control circuit 15 recognizes the observation mode through a changeover operation of the mode changeover switch 14. The control circuit 15 performs control of automatically modifying the processing contents of the emphasis circuit 48 to different processing contents in the WLI mode and NBI mode according to the observation mode based on the type of the CCD 29 and the observation mode.

Furthermore, according to a manual instruction by the user such as operator from a setting section 50 provided in the video processor 4, the control circuit 15 may also be adapted to be able to modify the amount of emphasis of the sharpness in response to the instruction.

The third matrix circuit 49 converts the inputted luminance signal Y and color difference signals R-Y and B-Y to three primary color signals R, G and B. The three primary color signals R, G and B generated by the third matrix circuit 49 are converted to analog video signals by a D/A conversion circuit (not shown) and outputted from a video signal outputted end to the monitor 5.

The third matrix circuit 49 is set in such a way that the matrix Mat3 becomes an inverse matrix of matrix Mat2 of the second matrix circuit 46 in the WLI mode.

To be more specific, when the matrix composed of matrix elements of three rows and three columns of the second matrix circuit 46 is assumed to be Mat2, if $Mat2^{-1}$ is expressed by an inverse matrix of matrix Mat2, matrix Mat3 in the WLI mode is set as:

$$Mat3 = Mat2^{-1} \tag{2a}$$

Regarding this matrix Mat2, as a matrix for converting RGB signals to Y color difference signal, the following publicly known calculation coefficient or the like are used.

[Equation 2]

$$Mat2 = \begin{bmatrix} 0.299 & 0.587 & 0.114 \\ 0.701 & -0.587 & -0.114 \\ -0.299 & -0.587 & 0.886 \end{bmatrix} \tag{2b}$$

On the other hand, in the NBI mode, when a matrix resulting from substituting 0, t and u for the matrix elements on the first row of above-described matrix Mat2 is represented by Mat2' and if

[Equation 3]

$$Mat2' = \begin{bmatrix} 0 & t & u \\ 0.701 & -0.587 & -0.114 \\ -0.299 & -0.587 & 0.886 \end{bmatrix}$$

is assumed, the third matrix circuit 49 is set in such a way that matrix Mat3 thereof becomes an inverse matrix of matrix Mat2' of the second matrix circuit 46.

When $Mat2'^{-1}$ is expressed by an inverse matrix of matrix Mat2', matrix Mat3 in the NBI mode is set as:

$$Mat3 = Mat2'^{-1} \tag{2c}$$

In the NBI mode, the first matrix circuit 42 is set to matrix Mat1 made up of matrix elements m21, ..., m33 as shown in Equation (3) below. Matrix elements m21, m22 and m23 on the first row become the same matrix elements on the second row, and the conversion output of the first row is the same as that of the second row.

[Equation 4]

$$Mat1 = \begin{bmatrix} m21 & m22 & m23 \\ m21 & m22 & m23 \\ m31 & m32 & m33 \end{bmatrix} \tag{3}$$

Furthermore, in the present embodiment, for example, a display color conversion setting section 50a is provided in the setting section 50 that makes settings for converting and displaying display colors so that an endoscope image may be displayed in colors in the NBI mode to be easily visually recognizable to the operator.

When the display color conversion function in the display color conversion setting section 50a is turned ON, the control circuit 15 performs control so as to use matrix Mat3 obtained by multiplying the inverse matrix of above-described matrix Mat2' by matrix $Mat_{NBI-C-Tf}$ that converts display colors.

In this case, matrix Mat3 is set as:

$$Mat3 = Mat_{NBI-C-Tf} Mat2'^{-1} \tag{4}$$

Here, when a matrix having matrix elements k1, k2 and k3 is assumed to be K, $Mat_{NBI-C-Tf}$ is expressed by:

[Equation 5]

$$Mat_{NBI-C-Tf} = K \tag{5}$$

$$= \begin{bmatrix} 0 & k1 & 0 \\ 0 & 0 & k2 \\ 0 & 0 & k3 \end{bmatrix}$$

When converting display colors by operating the display color conversion setting section 50a, the operator may be allowed to variably set the values of color conversion matrix elements k1, k2 and k3.

As described above, the present embodiment changes processing contents on emphasized signals as the image signals subjected to emphasis processing by the emphasis circuit 48 according to the observation mode. To be more specific, in the WLI mode, the emphasis circuit 48 performs emphasis processing of adding a result of convolutional calculation using digital filters (DC component=0) in a predetermined filter size to input signals (luminance signal Y and two color difference signals R-Y and B-Y) to the emphasis circuit 48 on the luminance signal Y and two color difference signals R-Y and B-Y.

For this purpose, the table 15b stores filter coefficients of the digital filters for performing emphasis processing by the emphasis circuit 48 for the WLI mode and for the NBI mode.

According to a unit array structure of a plurality of filter elements making up the color filter 30 as the aforementioned color separation section, a pixel density for generating the luminance signal Yh is greater than the pixel density for generating the color difference signals Cr' and Cb', and therefore filter coefficients are set as follows according to the array structure corresponding to the pixel density. That is, filter coefficients are set so as to have an emphasis characteristic having a greater amount of emphasis for an image signal with a high pixel density than for an image signal with a low pixel density. In other embodiments which will be described later, filter coefficients are also set according to the array structure basically corresponding to the pixel density of the color separation section.

Filter coefficient WLI-Y for a luminance signal, filter coefficient WLI-R-Y (that is, WLI-Cr) for a color difference signal R-Y and filter coefficient WLI-B-Y (WLI-Cb) for a color difference signal B-Y are stored as emphasis processing filter coefficients for the WLI mode. For the filter coefficients WLI-Cr and WLI-Cb for color difference signals, values obtained by multiplying all filter coefficients of the filter coefficient WLI-Y for a luminance signal by a constant ka (ka<1) are stored.

On the other hand, as emphasis processing filter coefficients for the NBI mode, filter coefficient NBI-Y for a luminance signal, filter coefficient NBI-R-Y (that is, NBI-Cr) for a color difference signal R-Y and filter coefficient NBI-B-Y (NBI-Cb) for a color difference signal are stored, and values equal to the filter coefficient WLI-Y for a luminance signal are stored for the filter coefficient NBI-Y for a luminance signal, filter coefficients of all zeros are stored for the filter coefficient NBI-Cr for a color difference signal, and values obtained by multiplying all filter coefficients of filter coefficient NB1-Y for a luminance signal by constant kb (kb<1) are stored for the filter coefficient NBI-Cb for a color difference signal.

Furthermore, in this case, constants ka and kb are set so as to be ka<kb, that is, the amount of emphasis for the color difference signal Cb in the NBI mode is greater (stronger) than that in the WLI mode.

Figure 4:
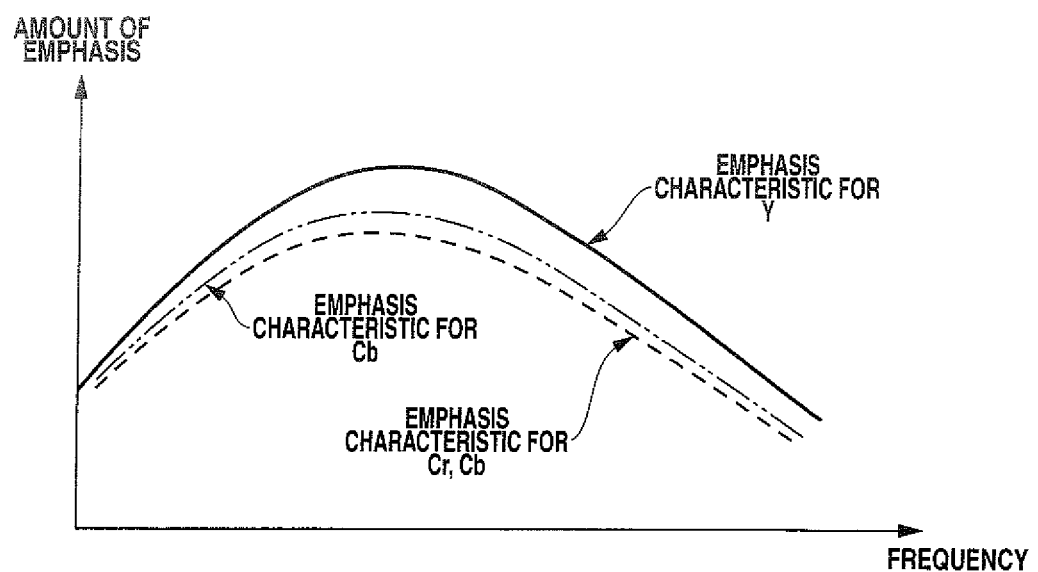
FIG. 4 is a diagram illustrating an example of emphasis characteristics for luminance and color difference signals of an emphasis circuit.

Therefore, an overview of an emphasis characteristic example when emphasis processing is performed by the emphasis circuit 48 using the above-described emphasis processing coefficients in the WLI mode and the NBI mode is as shown in FIG. 4. As shown in FIG. 4, a greater amount of emphasis is set for the luminance signal Y shown by a solid line than the color difference signals Cr, Cb shown by a dotted line over the entire frequency domain.

In the case of NBI, the amount of emphasis is set so as to have substantially the same tendency for the luminance signal Y and one color difference signal Cb. However, a relative emphasis characteristic of the color difference signal Cb with respect to the luminance signal Y is set to a characteristic that the amount of emphasis is greater than that in the WLI mode as described above. This situation is shown by a two-dot dashed line in FIG. 4.

The emphasis processing by the emphasis circuit 48 may also be adapted so that the emphasis characteristic thereof can be modified according to the type of the CCD 29 and color filter 30 or the like via the control circuit 15 according to an operation from the emphasis setting section in the setting section 50.

The endoscope apparatus 1 in the present embodiment in such a configuration includes the CCD 29 as image pickup means provided with the color filter 30 as a color separation section that color-separates, receives and picks up an image of returning light of light radiated onto a subject by illumination means and the emphasis circuit 48 as emphasis processing means for performing sharpness emphasis processing on an image signal based on the image pickup means.

Furthermore, the endoscope apparatus 1 includes the table 15b as storing means for storing information for modifying processing contents of the emphasis processing means according to the spectral characteristics of the returning light incident on the image pickup means which differ depending on the type of the image pickup means and observation mode, and the control circuit 15 as control means for performing control of modifying processing contents of the emphasis processing means based on the information of the storing means.

Figure 5:
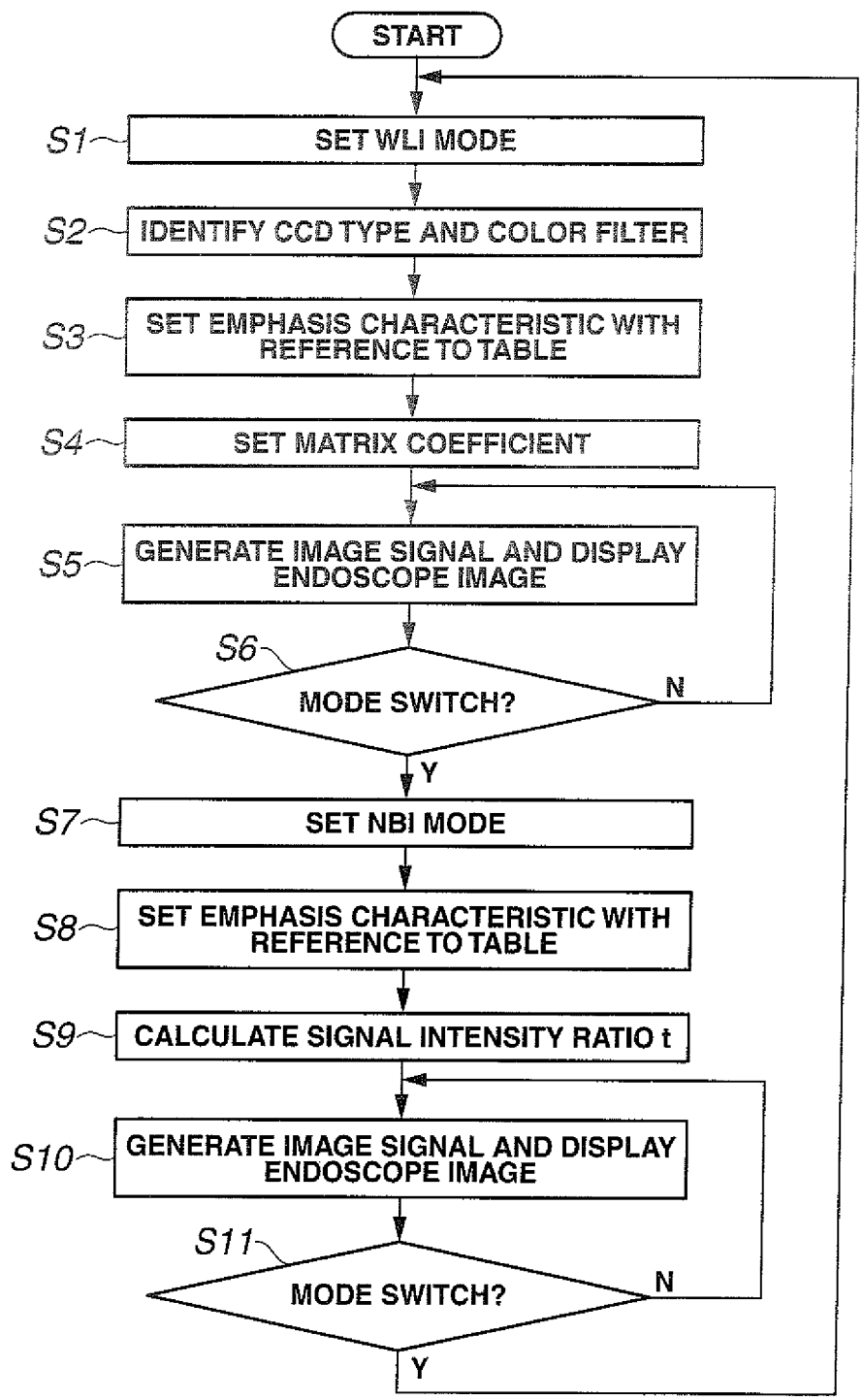
FIG. 5 is a flowchart for illustrating main operations according to the first embodiment.

Next, main operations of the present embodiment will be described below with reference to FIG. 5.

When the operator connects the endoscope 2 to the light source device 3 and the video processor 4 as shown in FIG. 1 and turns on the power, the control circuit 15 of the video processor 4 starts initial setup processing. As shown in step S1, the control circuit 15 causes the light source device 3 and the video processor 4 to be set, for example, in an operating mode corresponding to the observation mode of the WLI mode. The control circuit 15 may also cause the light source device 3 and the video processor 4 to be set in an observation mode instructed by the operator.

When the WLI mode is set, the light source device 3 is set in a state in which the narrow band filter 24 is separated from the illuminating light path as shown by a solid line in FIG. 1 and the endoscope 2 is set to perform image pickup under white illuminating light. Furthermore, the sections on the video processor 4 side are also set to perform signal processing in the WLI mode.

As shown in step S2, the control circuit 15 identifies, using the ID from the ID generation section 33, the type of the image pickup means, that is, identifies that the type of the CCD 29 is a single CCD and the color filter 30 of the CCD 29 is a single CCD complementary color filter.

Then, as shown in step S3, with reference to the table 15b using information on the observation mode and the type of the CCD 29, the control circuit 15 sets filter coefficients used when performing emphasis processing through the emphasis circuit 48, that is, sets an emphasis characteristic.

The emphasis circuit 48 whose filter coefficients are set in this way has an emphasis characteristic as shown in FIG. 4. As shown in FIG. 4, the luminance signal is set to have a greater amount of emphasis than the color difference signal. With such a setting, when sharpness is emphasized so that edges of a living tissue or the like becomes clearer, since the emphasis characteristic corresponding to a pixel density is set, it is possible to lay emphasis while suppressing the occurrence of false color or color moire.

Furthermore, as shown in step S4, with reference to the table 15a, the control circuit 15 sets matrix coefficients for performing matrix calculations using the first matrix circuit 42, the second matrix circuit 46 and the third matrix circuit 49 respectively.

As shown in step S5, the video processor 4 performs image processing using the above-described filter coefficients and matrix coefficients, generates three primary color signals R, G and B as image signals of an endoscope image via the third matrix circuit 49 and outputs them to the monitor 5. The monitor 5 displays the endoscope image as an observed image corresponding to the image signals. The operator performs an endoscope inspection of a tissue to be examined such as diseased part in the body cavity while observing this endoscope image.

In next step S6, the control circuit 15 monitors whether or not a mode changeover operation has been carried out. When the mode changeover operation has not been carried out, the process returns to step S5 and the process of displaying the endoscope image in the WLI mode continues.

When attempting to observe the running state or the like of a blood vessel on the surface of the tissue to be examined in detail, the operator operates the mode changeover switch 14.

When the mode changeover switch 14 is operated, the control circuit 15 modifies the observation mode of the light source device 3 and video processor 4 to the NBI mode as shown in step S7.

To be more specific, the control circuit 15 controls the light source device 3 so as to place the narrow band filter 24 in the illuminating light path as shown by a two-dot dashed line in FIG. 1. When the narrow band filter 24 is placed in the illuminating light path, whose transmission characteristic is shown in FIG. 2, illumination is performed using narrow band illuminating light with narrow band pass filter characteristic parts Ga and Ba.

Furthermore, the control circuit 15 modifies settings of the sections of the video processor 4. To be more specific, the control circuit 15 widens the band characteristic of the LPF 41b.

Furthermore, the control circuit 15 widens the signal passband characteristic of the LPF 41b and improves the resolution of the running state of the capillary vessel and the blood vessel running state or the like close to the surface layer obtained by the color signal of G, an image of which is picked up under illuminating light of G close to the luminance signal by the narrow band pass filter characteristic part Ga as described above.

Furthermore, in next step S8, the control circuit 15 refers to the table 15b as the mode is changed to the NBI mode and sets a filter coefficient used when performing emphasis processing through the emphasis circuit 48, that is, sets the emphasis characteristic.

The emphasis circuit 48 whose filter coefficient is set in this way has an emphasis characteristic as shown in FIG. 4. The amount of emphasis of the luminance signal Y is set to be greater than that of the color difference signal Cb in both the NBI mode and WLI mode. As in the case of the WLI mode, such a setting makes it possible to place emphasis while suppressing the occurrence of false color or color moire. Moreover, since the amount of emphasis of the color difference signal is set to be greater than in the WLI mode, it is easier to identify contours and edges or the like of a blood vessel.

Furthermore, in step S9, the signal intensity ratio calculation circuit 45 calculates a signal intensity ratio t. The control circuit 15 sets matrix coefficients for performing matrix calculations using the first matrix circuit 42, the second matrix circuit 46 and the third matrix circuit 49 with reference to the values of the calculated signal intensity ratio t and the table 15a.

As shown in step S10, the video processor 4 performs image processing using the above-described filter coefficients and matrix coefficients, generates three primary color signals R, G and B as image signals of the endoscope image through the third matrix circuit 49 and outputs the three primary color signals R, G and B to the monitor 5. The monitor 5 displays the endoscope image as an observed image corresponding to the image signals.

When the display color conversion setting section 50a is OFF, the third matrix circuit 49 generates color signals R, G and B as three primary color signals not to be subjected to display color conversion, and when the display color conversion setting section 50 is ON, the third matrix circuit 49 generates three primary color signals R, G and B subjected to display color conversion.

The operator performs an endoscope inspection while observing this endoscope image in a condition in which the running state of the capillary vessel or the like close to the surface of a tissue to be examined in the body cavity can be easily identified in more detail.

In next step S11, the control circuit 15 monitors whether or not a mode changeover operation has been performed. When the mode changeover operation has not been performed, the process returns to step S10 and continues the process of displaying the endoscope image in the NBI mode.

On the other hand, when the mode changeover operation has been performed, the process returns to step S1.

According to the present embodiment that operates in this way, the emphasis circuit 48 can perform emphasis processing while suppressing the occurrence of false color or color moire. Therefore, the present embodiment can provide an endoscope image as an observed image of high quality, allowing the operator to easily make a diagnosis or the like.

Furthermore, since the present embodiment adopts a high frequency band for the signal band of the color difference signal also in the NBI mode, it is possible to obtain a high resolution endoscope image and display the running state of the capillary vessel or the like in a more clearly and easily identifiable condition.

Furthermore, the present embodiment adopts a configuration of generating an image signal through matrix calculation in the third matrix circuit 49 according to the signal intensity ratios t and u of the color signals G1 and B1 in the NBI mode, and can thereby convert a luminance signal to a color signal according to the signal intensities of the color signals G1 and B1 and prevent deterioration of the contrast of the endoscope image in the NBI mode.

Furthermore, the present embodiment can easily support both the WLI mode and NBI mode by changing part of processing characteristics in the signal processing system (image processing system), and can thereby provide a highly convenient and useful apparatus during an endoscope inspection.

Furthermore, by providing means for inserting/removing the narrow band filter 24 in/from the optical path in addition to illumination means of normal white light, the light source device 3 can also easily form a light source device of narrow band light.

Figure 6:
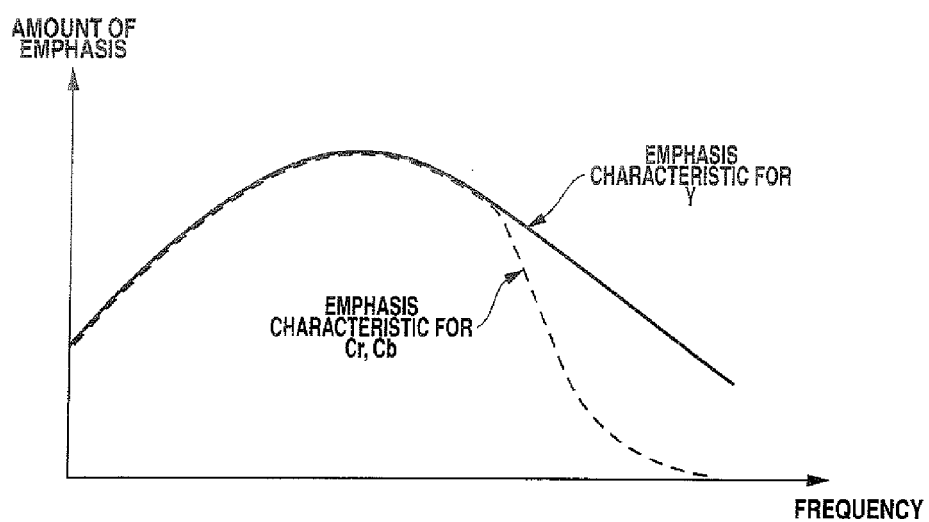
FIG. 6 is a diagram illustrating an example of emphasis characteristics of an emphasis circuit according to a modification example.

In the aforementioned first embodiment, the emphasis characteristic of the emphasis circuit 48 is set as shown in FIG. 4, but an emphasis characteristic as shown in FIG. 6 may also be set as a modification example of the emphasis characteristic.

As for the luminance signal Y, the emphasis characteristic shown in FIG. 6 is set to an emphasis characteristic similar to that shown in FIG. 4 in both the WLI mode and the NBI mode, while as for the color difference signals Cr and Cb (in WLI mode) or Cb (in NBI mode), filter coefficients are set so as to have frequency characteristics in which the amount of emphasis is smaller on the high frequency band side having a higher frequency.

Adopting such a frequency characteristic makes it possible to reduce the occurrence of color moire which becomes conspicuous on the high frequency band side.

As a modification example, it may be possible to designate only the luminance signal Y as an emphasized signal and emphasize only the luminance signal Y through the emphasis circuit 48 in the WLI mode, while in the NBI mode, it may be possible to designate the luminance signal Y and the color difference signal Cb as emphasized signals and emphasize the luminance signal Y and the color difference signal Cb through the emphasis circuit 48.

Furthermore, as another modification example, it may be possible to adopt three-peak spectral characteristics for the narrow band filter, further have a narrow band pass filter characteristic part Ra (center wave length of 600 nm and full width at half maximum of 20 to 40 nm) and designate the luminance signal Y and the color difference signals Cb (B-Y) and Cr (R-Y) as emphasized signals in the NBI mode, and perform emphasis processing on the luminance signal Y and the color difference signals Cb and Cr through the emphasis circuit 48 so that the emphasis characteristic is weaker with the color difference signals Cb and Cr than the luminance signal Y and the same between the color difference signals Cb and Cr.

First Modification Example of First Embodiment

Figure 7:
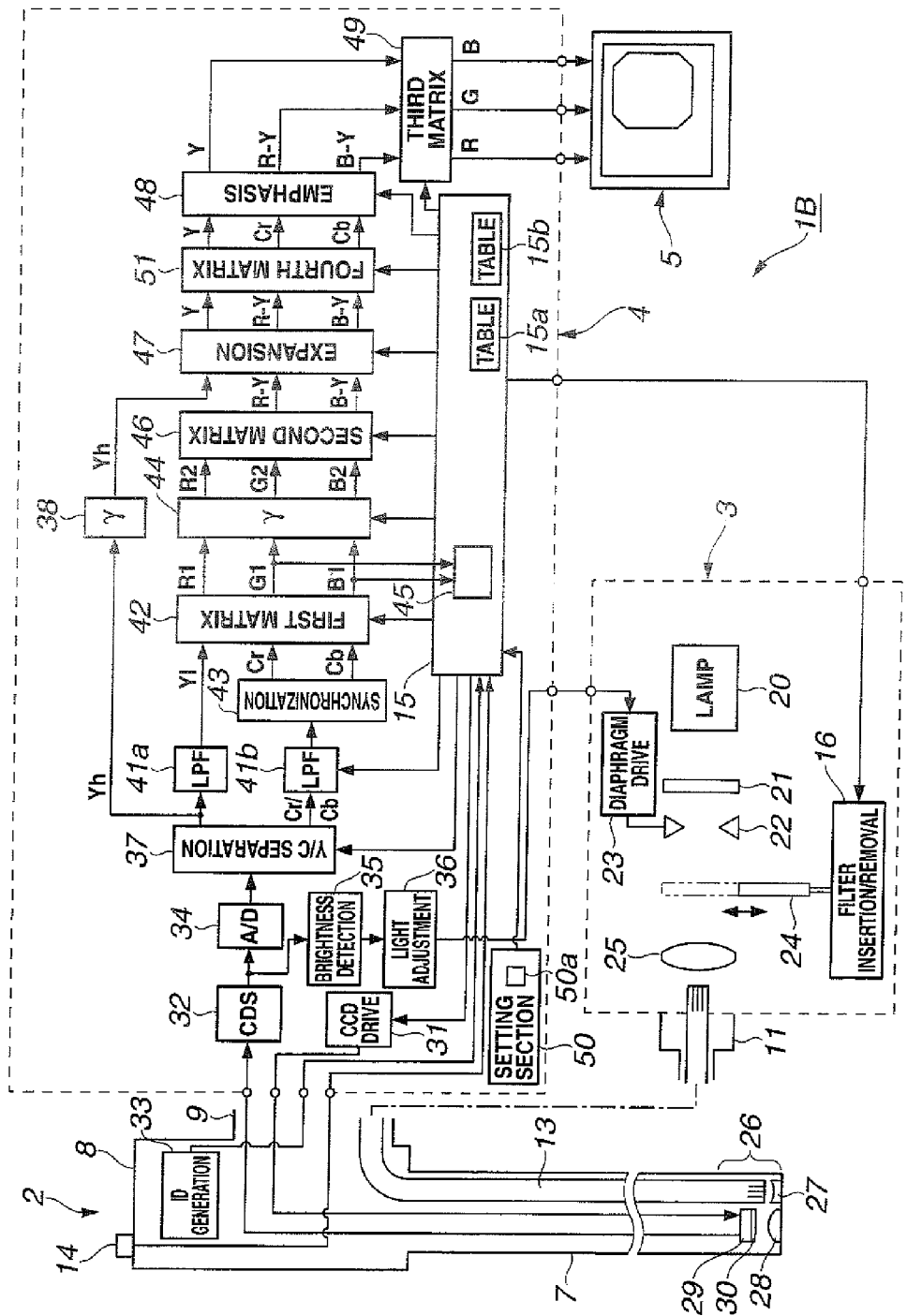
FIG. 7 is a block diagram illustrating a configuration of an endoscope apparatus in a modification example of the first embodiment.

FIG. 7 shows an overall configuration of an endoscope apparatus 1B according to a first modification example of the first embodiment of the present invention. The present modification example has a configuration in which a fourth matrix circuit 51 is provided before the emphasis circuit 48 in the video processor 4 in the first embodiment shown in FIG. 1.

The fourth matrix circuit 51 performs a matrix calculation of generating emphasized signals Y, Cr and Cb having a high color moire reduction effect on the luminance signal Y and color difference signals R-Y and B-Y outputted from the expansion circuit 47 and inputted to the fourth matrix circuit 51 using matrix Mat4.

That is, when emphasized signals which are signals inputted to the emphasis circuit 48 are represented by Y, Cr and Cb as described above, the fourth matrix circuit 51 converts them as shown in Equation (6) and adopts matrix Mat4 as shown in Equations (7) and (8) in the WLI mode and the NBI mode respectively.

[Equation 6]

$$\begin{bmatrix} Y \\ Cr \\ Cb \end{bmatrix} = Mat4 \cdot \begin{bmatrix} Y \\ R-Y \\ B-Y \end{bmatrix} \quad (6)$$

$$Mat4 = \begin{bmatrix} 1 & 0 & 0 \\ 0 & a & 0 \\ 0 & 0 & b \end{bmatrix} (WLI \text{ mode}) \quad (7)$$

$$Mat4 = \begin{bmatrix} 1 & 0 & 0 \\ 0 & 0 & 0 \\ 0 & 0 & c \end{bmatrix} (NBI \text{ mode}) \quad (8)$$

where, a, b, c ≤ 1

Matrix Mat3 by the third matrix circuit 49 in the present embodiment is set to:

$$Mat3 = Mat2^{-1} \quad (9)$$

in the same way as in the first embodiment in the WLI mode. On the other hand, unlike the first embodiment, matrix Mat3 in the NBI mode is set to:

$$Mat3 = Mat_{NBI\text{-}C\text{-}Tf} Mat41NBI^{-1} \quad (10)$$

Here, matrix $Mat41_{NBI}$ is expressed by:

[Equation 11]

$$Mat41_{NBI} = \begin{bmatrix} m11 & m12 & m13 \\ 0.701 & -0.587 & -0.114 \\ -0.299 & -0.587 & 0.886 \end{bmatrix} \quad (11)$$

Matrix elements m11, m12 and m13 are predetermined values. The matrix elements m11, m12 and m13 are set based on signal intensity ratios between R, G and B in the luminance signal Yh. Alternatively, m12=t, m13=u and m11=0 are set using the signal intensity ratios t and u calculated by the aforementioned signal intensity ratio calculation circuit 45.

The rest of the configuration is similar to that of the first embodiment. The present modification example generates an emphasized signal having a high color moire reducing effect and performs emphasis processing through the emphasis circuit 48, and can thereby reduce color moire more than the first embodiment. In other aspects, the present modification example has operations and effects similar to those of the first embodiment.

When the fourth matrix circuit 51 performs conversion as shown in Equation (6), the conversion may be performed as shown in the following second modification example.

In the second modification example, in the NBI mode, Mat4 may be expressed by the following equation instead of Equation (8):

$$Mat4 = Mat42_{NBI} Mat41_{NBI}^{-1} \quad (12)$$

where, $Mat42_{NBI}$ is expressed by:

[Equation 13]

$$Mat42_{NBI} = \begin{bmatrix} m11 & m12 & m13 \\ 0 & 0 & 0 \\ m31 & m32 & m33 \end{bmatrix} \quad (13)$$

where the matrix elements m31, m32 and m33 are predetermined values. The matrix elements m31, m32 and m33 are values that satisfy m11*m31+m12*m32+m13*m33=0. $Mat41_{NBI}$ is expressed by Equation (11).

Furthermore, in this case, as in the case of the first embodiment, matrix Mat3 of the third matrix circuit 49 in the WLI mode is set to:

$$Mat3 = Mat2^{-1} \quad (14)$$

On the other hand, unlike the first embodiment, Mat3 in the NBI mode is set as:

$$Mat3 = Mat_{NBI\text{-}C\text{-}Tf} Mat42_{NBI}^{-1} \quad (15)$$

Matrix $Mat_{NBI\text{-}C\text{-}Tf}$ is expressed by Equation (5). Matrix $Mat42_{NBI}^{-1}$ is not limited to the case with an inverse matrix of $Mat42_{NBI}$ expressed by Equation (13).

For example, suppose a pseudo-inverse matrix (3 rows, 2 columns) of a matrix (2 rows, 3 columns) composed of the first and third row elements of matrix $Mat42_{NBI}$ may be derived and a matrix of 3 rows and 3 columns (all elements of the second column are 0) whose first and second column elements are designated as their respective first and third column elements may be used. This second modification example has operations and effects substantially the same as those of the first modification example.

Second Embodiment

Figure 8:
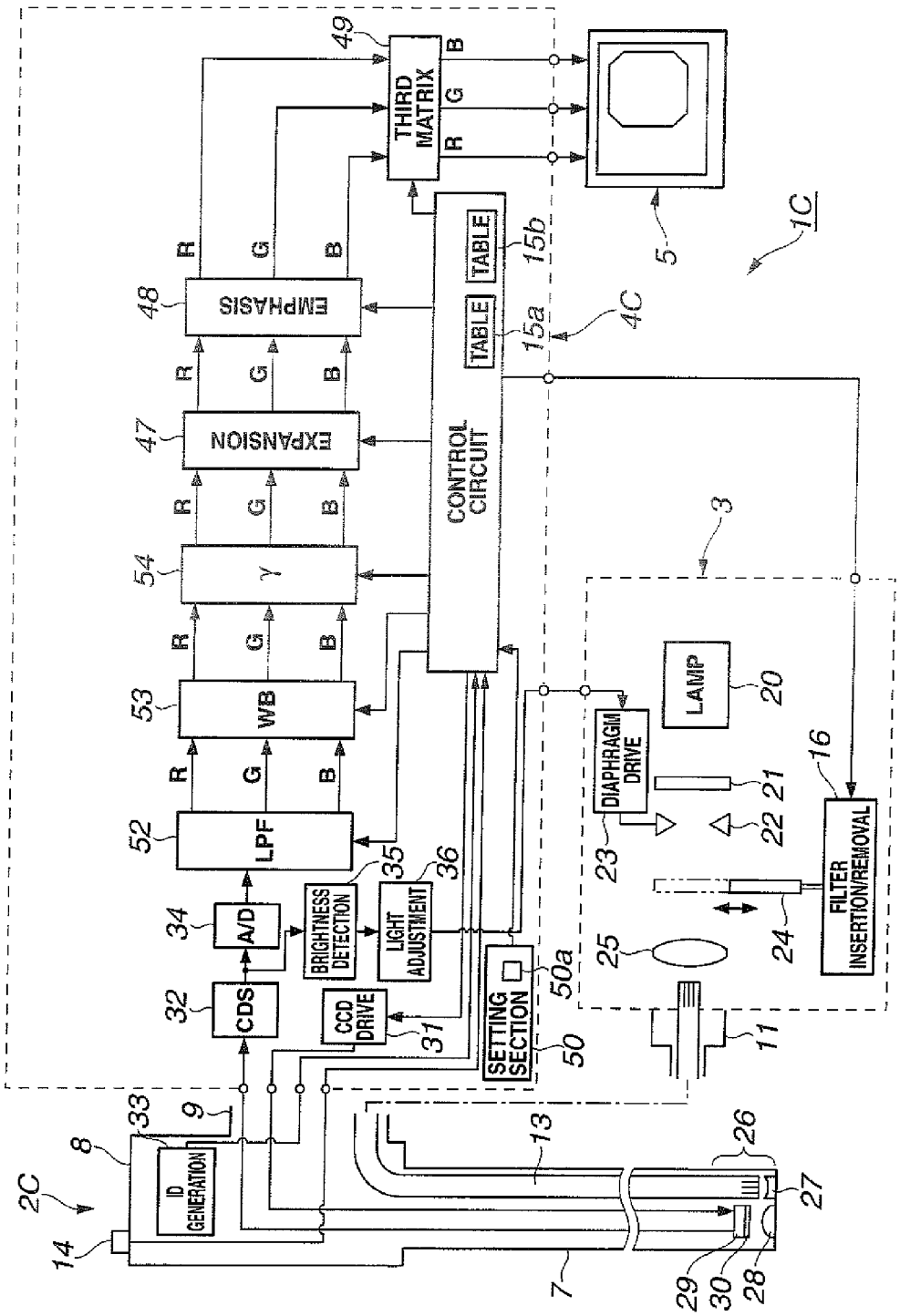
FIG. 8 is a block diagram illustrating a configuration of an endoscope apparatus according to a second embodiment of the present invention.

FIG. 8 shows an overall configuration of an endoscope apparatus 1C according to a second embodiment of the present invention. The endoscope apparatus 1C is made up of an endoscope 2C, a light source device 3, a video processor 4C and a monitor 5.

Figure 9:
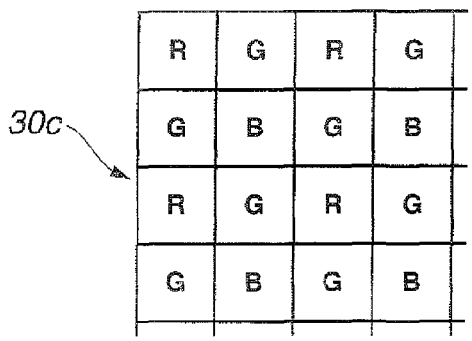
FIG. 9 is a diagram illustrating a filter array of a color filter according to the second embodiment.

For the endoscope 2C, for example, an image pickup device with a primary color single CCD is adopted instead of the image pickup device with complementary color single CCD in the endoscope 2 in FIG. 1. That is, a color filter 30c with a primary color single CCD Bayer array as shown in FIG. 9 is adopted for the image pickup surface of the CCD 29.

This color filter 30c has a filter array in which a unit of four filter elements of two rows and two columns in the horizontal and vertical directions is periodically arranged in the horizontal and vertical directions. In this case, color filter elements of R, G and G, B are alternately arranged in the horizontal and vertical directions.

The CCD 29 is driven by the CCD drive circuit 31 in the same way as, for example, in the first embodiment. The video processor 4C in this case has a configuration in which the output signal of the A/D conversion circuit 34 in the video processor 4 in FIG. 1 is inputted to the LPF 52 via a changeover circuit (not shown) that switches between output signals in pixel units.

By passing through the LPF 52, missing pixel values of color signals at each pixel position are calculated, and synchronized three primary color signals R, G and B are generated. The three primary color signals R, G and B generated after passing through the LPF 52 are subjected to white balance processing through a white balance circuit (abbreviated to "WB circuit") 53 and then inputted to a γ circuit 54 that performs gamma correction.

The three primary color signals R, G and B outputted from the γ circuit 54 are inputted to an expansion circuit 47 as in the case of the configuration of the video processor 4 in FIG. 1, subjected to expansion processing and inputted to an emphasis circuit 48 that performs sharpness emphasis processing on the three signals.

After being subjected to emphasis processing through the emphasis circuit 48, the three signals are generated into three primary color signals R, G and B by a third matrix circuit 49 as an image signal of the endoscope image as an observed image and outputted to the monitor 5.

According to the present embodiment, in the WLI mode, the emphasized signals are three primary color signals R, G and B and the emphasis circuit 48 performs emphasis processing on the three primary color signals R, G and B as the emphasized signals. As for the amount of emphasis in this case, WLI filter coefficients are stored in a table 15b so that the amount of emphasis on G becomes greater than the amounts of emphasis on other R and B.

On the other hand, in the NBI mode, the emphasized signals are (two color signals in) three primary color signals G and B, and the emphasis circuit 48 performs emphasis processing on the (color signals as) emphasized signals G and B. As for the amount of emphasis in this case, NBI filter coefficients are stored in the table 15b so that the amount of emphasis on G is greater than the amount of emphasis on other B.

That is, the table 15b stores WLI-RB filter coefficients and WLI-G filter coefficients as WLI filter coefficients, and stores NBI-B filter coefficients and NBI-G filter coefficients as NBI filter coefficients.

The WLI-RB filter coefficients and the NBI-B filter coefficients are set to values obtained by multiplying all the WLI-G filter coefficients and NBI-G filter coefficients by constant ka (ka<1).

The present embodiment sets common constant ka in the WLI mode and NBI mode, but constants ka and kb may be set in the WLI mode and NBI mode so as to be ka<kb as in the first embodiment.

Furthermore, in the present embodiment, the third matrix circuit 49 performs matrix calculation using a unit matrix in the WLI mode. On the other hand, the third matrix circuit 49 performs matrix calculation using matrix $Mat_{NBI-C-Tf}$ shown in aforementioned Equation (5) in the NBI mode. That is, when input/output signals RGB to/from the third matrix circuit 49 are assumed to be Rin, Gin, Bin, Rout, Gout and Bout, the third matrix circuit 49 performs the following matrix calculation.

[Equation 16]

$$\begin{bmatrix} Rout \\ Gout \\ Bout \end{bmatrix} = Mat_{NBI-C-Tf} \cdot \begin{bmatrix} Rin \\ Gin \\ Bin \end{bmatrix}$$

The table 15a stores matrix coefficients used in the third matrix circuit 49.

Operation of the present embodiment in such a configuration is different in the emphasized signals from the first embodiment, but the basic operation thereof is similar to that of the first embodiment.

Since the emphasis circuit 48 of the present embodiment is also set to an emphasis characteristic corresponding to the pixel density, the emphasis circuit 48 can perform emphasis processing while suppressing the occurrence of false color or color moire. Therefore, according to the present embodiment, it is possible to provide an endoscope image as an observed image of high quality allowing the operator to easily make a diagnosis or the like.

Furthermore, the present embodiment does not apply band limitation even in the NBI mode, and can thereby obtain an endoscope image of high resolution and display the running state of a capillary vessel or the like in a more clearly and easily identifiable condition.

Furthermore, the present embodiment can easily support both the WLI mode and NBI mode by changing part of processing characteristics in the signal processing system, and can thereby provide a highly convenient and useful apparatus during an endoscope inspection.

A case of an image pickup device with a primary color single CCD has been described in the present embodiment, but an image pickup device with a primary color double CCD, that is, an image pickup section made up of two image pickup devices may also be adopted.

Figure 10:
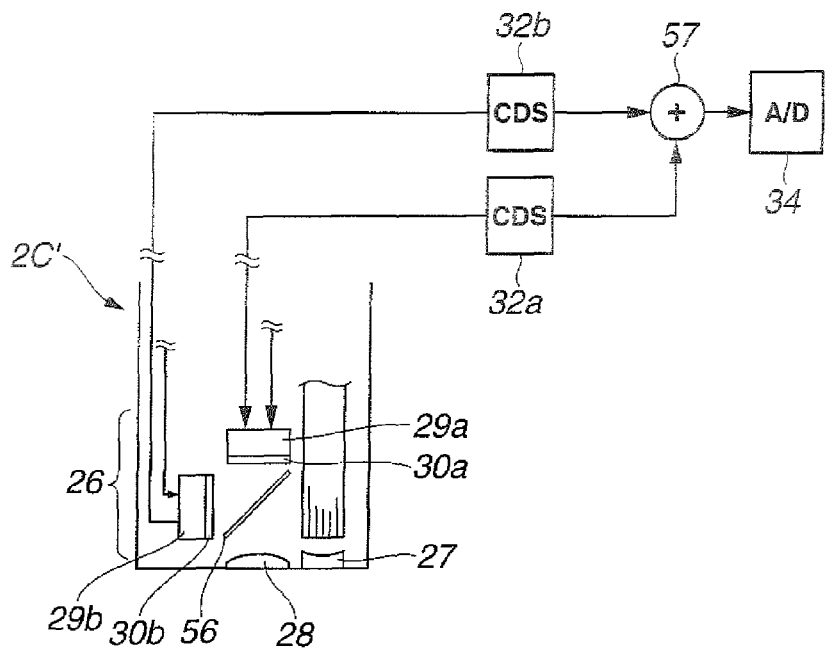
FIG. 10 is a diagram illustrating a configuration of a periphery of a double CCD image pickup section provided at a distal end portion of the endoscope.

FIG. 10 shows a configuration of a periphery of the image pickup section at a distal end portion 26 of an endoscope 2C' in this case. A first CCD 29a is arranged at an image forming position on the optical axis of an objective lens 28. A half mirror 56 which passes and reflects substantially 50% of incident light is placed at some midpoint on the optical axis.

A second CCD 29b is placed at an image forming position on the optical axis of light reflected by the half mirror 56.

Figure 11:
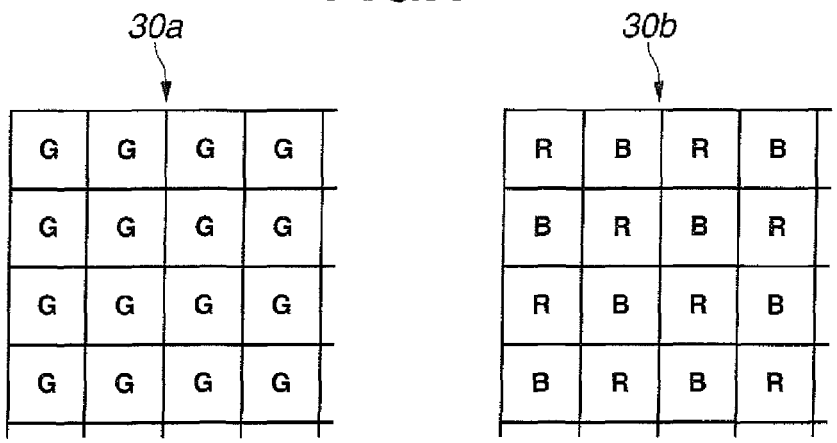
FIG. 11 is a diagram illustrating a filter array of a color filter used for the double CCD image pickup section.

Color filters 30a and 30b with primary colors as shown in FIG. 11 are arranged on the image pickup surfaces of the first CCD 29a and the second CCD 29b as color separation sections.

The color filter 30a is made up of only Gs as filter elements. On the other hand, the color filter 30b is made up of Rs and Bs as filter elements.

A unit array structure for generating color signals for performing color image pickup using both the color filters 30a and 30b corresponds to pixels of two rows and two columns and color signals generated from unit pixels are 4Gs+2(R+B)s. In the case of the color filter 30c in FIG. 9, color signals generated from pixels of two rows and two columns corresponding to the unit array for generating color signals are 2Gs+R+B. The first CCD 29a and the second CCD 29b are driven by a common CCD drive circuit 31. Furthermore, the output signals of the first CCD 29a and second CCD 29b are converted to baseband signal components by CDS circuits 32a and 32b respectively.

The output signals of the CDS circuits 32a and 32b are subjected to gain adjustment for correcting characteristics of the half mirror 56 by an amplifier (not shown), and then added up by an adder 57 and inputted to the A/D conversion circuit 34 shown in FIG. 8.

The signal inputted to the A/D conversion circuit 34 is a signal at resolution twice as high as that in the case of FIG. 8. The processing after the A/D conversion circuit 34 is the same as that in FIG. 8.

According to the present modification example, it is possible to generate an endoscope image with higher resolution. Other operations and effects are the same as those of the second embodiment.

Furthermore, as a modification example of the above-described second embodiment and a modification example of the modification example, filter coefficients may be set such that the amount of emphasis of the color signal G is greater than those of the color signal R and B (in WLI mode) or B (in NBI mode) only on the high frequency side instead of making the amount of emphasis of the color signal G greater than those of the color signals R and B (in WLI mode) or B (in NBI mode).

Furthermore, in the embodiment shown in FIG. 8, the emphasis circuit 48 is configured to perform emphasis processing on the color signals R, G and B (in WLI mode) or G and B (in NBI mode), but a configuration may also be adopted in which those signals are converted to a luminance signal Y and color difference signals Cr and Cb and the emphasis circuit 48 performs emphasis processing on the converted luminance signal Y and color difference signals Cr and Cb.

Third Embodiment

Figure 12:
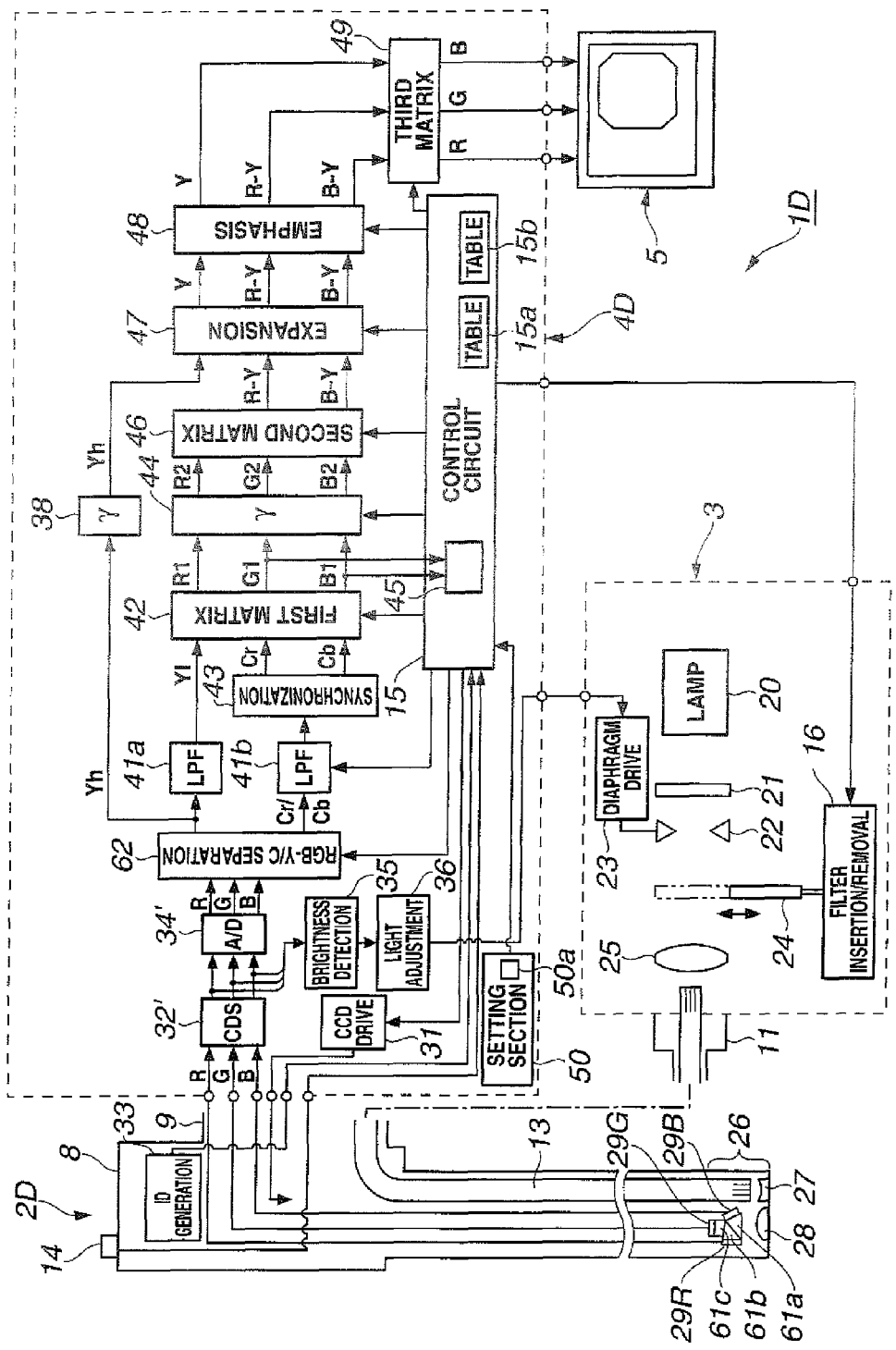
FIG. 12 is a block diagram illustrating a configuration of an endoscope apparatus according to a third embodiment.

FIG. 12 shows an overall configuration of an endoscope apparatus 1D according to a third embodiment of the present invention. This endoscope apparatus 1D is made up of an endoscope 2D, a light source device 3, a video processor 4D and a monitor 5. The endoscope 2D is mounted with an image pickup section made up of an image pickup device with a primary color triple CCD instead of the (image pickup section made up of) one image pickup device placed at the distal end portion 26 of the insertion portion 7 in the endoscope 2 in FIG. 1.

Color separation prisms 61a, 61b and 61c as a color separation section to perform color separation into R, G and B and three CCDs 29R, 29G and 29B arranged at their respective image forming positions are provided on the optical axis of the objective lens 28. Therefore, in this case, the three CCDs 29R, 29G and 29B each output R, G and B color signals in pixel units. The present embodiment corresponds to a unit array in the case where one pixel performs color image pickup.

Therefore, in the case of the present embodiment, as shown in FIG. 13, signals color-separated into R, G and B in pixel units are outputted. Without being limited to the configuration example of the image pickup device with a primary color triple CCD having the structure shown in FIG. 12, a triple CCD image pickup device in which color-separating primary color filters as shown in FIG. 13 are attached to image pickup surfaces of three CCDs may also be used.

The above-described CCDs 29R, 29G and 29B are driven by a common CCD drive circuit 31.

Furthermore, output signals of the CCD 29R, 29G and 29B are inputted to a three-line CDS circuit 32' and baseband color signals R, G and B are outputted from this CDS circuit 32' to a three-line A/D conversion circuit 34' and a brightness detection circuit 35.

The digital color signals R, G and B, which are A/D-converted by the A/D conversion circuit 34', are inputted to an RGB-Y/C separation circuit 62 and converted to a luminance signal Y and color difference signals Cr and Cb.

The processing configuration corresponding to the luminance signal Y and color difference signals Cr and Cb as the output signals from the RGB-Y/C separation circuit 62 and the rest is similar to the configuration example shown in FIG. 1. However, as shown below, the emphasis characteristic of the emphasis circuit 48 is different from that in FIG. 1.

A table 15b stores filter coefficients for emphasis processing by the emphasis circuit 48 in the present embodiment, too.

In the present embodiment, WLI-Y/Cr/Cb filter coefficients and NBI-Y/Cb filter coefficients are stored as filter coefficients for emphasis processing and to be stored in the table 15b, and the same values are stored as all the WLI-Y/Cr/Cb filter coefficients and NBI-Y/Cb filter coefficients (NBI-Cr filter coefficients are zero). Since the pixel density, that is, the pixel density when color signals R, G and B are generated is the same, the present embodiment is also set so as to have emphasis characteristics corresponding to the same value.

The control circuit 15 sets filter coefficients for emphasis processing by the emphasis circuit 48 with reference to the table 15b for each observation mode.

Furthermore, the table 15a stores matrix coefficients of the first matrix circuit 42, the second matrix circuit 46 and the third matrix circuit 49 as in the case of the first embodiment. Matrix calculations similar to those in the first embodiment are performed.

Operation in the present embodiment is similar to the operation of the image pickup section made up of a single CCD image pickup device provided with a complementary color filter of the first embodiment substituted by an image pickup section made up of an image pickup device with a primary color triple CCD.

However, unlike the first embodiment, the present embodiment performs emphasis processing with the same emphasis characteristic on the luminance signal Y and the color difference signals Cr and Cb in correspondence with the image pickup device with a primary color triple CCD.

Performing emphasis processing corresponding to the image pickup device with a primary color triple CCD in this way makes it possible to improve reproducibility of a blood vessel image through emphasis processing. Furthermore, use of the image pickup device with a primary color triple CCD makes it possible to obtain an endoscope image with higher resolution than that in the first embodiment.

As a modification example of the present embodiment, a configuration may be adopted in which the output signal of the A/D conversion circuit 34' in FIG. 12 is outputted to the WB circuit 53 in FIG. 8.

In that case, WLI-RGB filter coefficients and NBI-GB filter coefficients are stored as filter coefficients for emphasis processing to be stored in the table 15b and the same values are stored for all WLI-RGB filter coefficients and NBI-GB filter coefficients (NBI-R filter coefficients are zeros).

The control circuit 15 sets filter coefficients to be subjected to emphasis processing by the emphasis circuit 48 with reference to the table 15b for each observation mode. The table 15a stores matrix coefficients of the first matrix circuit 42, the second matrix circuit 46 and the third matrix circuit 49 as in the case of the second embodiment. Matrix calculations similar to those in the second embodiment are performed.

The configuration in the present modification example is different in emphasized signals but has operations and effects similar to those of the third embodiment. That is, since the present modification example also performs emphasis processing corresponding to the image pickup device with a primary color triple CCD, it is possible to improve reproducibility of blood vessel images or the like through emphasis processing in the same way as in the aforementioned third embodiment. Furthermore, use of the image pickup device with a primary color triple CCD allows an endoscope image with high resolution to be obtained.

Fourth Embodiment

Cases in the WLI mode and the NBI mode have been described in the aforementioned embodiments. The present invention is however not limited to cases in the WLI mode and the NBI mode as in the aforementioned embodiments, but is also applicable to cases in at least one observation mode of the WLI mode and the NBI mode and a fluorescent mode in which fluorescent observation is performed. As the fluorescent mode in which fluorescent observation is performed, fluorescent observation is performed in a green to red region or a green to near-infrared region.

In the case of this fluorescent mode, emphasized signals are emphasized as shown in the field of the amount of emphasis according to the image pickup section (image pickup device) being the complementary color single CCD, primary color single CCD, double CCD or primary color triple CCD as shown in FIG. 14. In this case, it is also possible to improve reproducibility of the biological mucous membrane while reducing the occurrence of false color or color moire and acquire an endoscope image easy to diagnose.

When the image pickup section is, for example, a primary color single CCD or double CCD, emphasis processing is performed with respect to color signals G and R so that the amount of emphasis of the color signal G is greater than the amount of emphasis of the color signal R.

In this case, as shown in the remarks field, after converting the color signals G and R to a luminance signal Y and a color difference signal Cr, the emphasis circuit 48 may perform emphasis processing so that the amount of emphasis of the luminance signal Y is greater than the amount of emphasis of the color difference signal Cr.

Furthermore, when the image pickup section is a primary color triple CCD, emphasis processing is performed on the color signals G and R in the case of primary color single CCD or double CCD so that the amount of emphasis of the color signal G is equal to the amount of emphasis of the color signal R. Furthermore, in this case, as shown in the remarks field, after converting the color signals G and R to a luminance signal Y and a color difference signal Cr, the emphasis circuit 48 may perform emphasis processing so that the amount of emphasis of the luminance signal Y is equal to the amount of emphasis of the color difference signal Cr.

Instead of setting the amount of emphasis as shown in FIG. 14 over the entire frequency region, filter coefficients whose amount of emphasis is reduced only in a high-frequency region may be set. In such a case, it is also possible to improve reproducibility of the biological mucous membrane while reducing the occurrence of false color due to color moire and obtain an endoscope image easy to diagnose.

Furthermore, when images of reflected light of blue color light and fluorescent light of red color light are picked up and endoscope images are generated as observed images in the first observation mode in other observation modes, emphasized signals may be emphasized according to the complementary color single CCD, primary color single CCD, double CCD and triple CCD as shown in the field of the amount of emphasis as shown in FIG. 15.

Furthermore, as a second observation mode in other observation modes, when an image of blue color light is picked up and an endoscope image is generated as an observed image, only one emphasized signal Y or B may be emphasized according to the complementary color single CCD, primary color single CCD, double CCD, triple CCD as shown in FIG. 16. In the case of FIG. 16, since the field of the amount of emphasis indicating the relationship of the amount of emphasis with a plurality of emphasized signals is unnecessary, the item is expressed as "–".

Furthermore, when an image of red color light is picked up and an endoscope image is generated as an observed image as a third observation mode in other observation modes, emphasized signals may be emphasized as shown in the field of amount of emphasis according to the complementary color single CCD, primary color single CCD, double CCD and triple CCD as shown in FIG. 17.

Furthermore, features of incident light, emphasized signal and de-emphasized signal reducing for which the amount of emphasis is reduced or the like in all the aforementioned embodiments can be summarized as shown in FIG. 18.

In FIG. 18, when, for example, incident light on the image pickup section or illuminating light by illumination means is white, in the case of a complementary color single CCD or primary color single CCD, the emphasized signal is a luminance signal Y, color difference signals Cr, Cb, a setting is made so as to reduce the amount of emphasis of the color difference signals Cr, Cb (with respect to the amount of emphasis of the luminance signal Y) in this case.

The case with a primary color double CCD is the same as the case with a complementary color single CCD or primary color single CCD on the left indicated by "←". Furthermore, in the case of a primary color triple CCD, emphasized signals are color signals R, G and B, a setting is made so that there are no signals for which the amount of emphasis is reduced the amount of emphasis in this case (in other words, set so that the amounts of emphasis of R, G and B signals are the same). Other cases are also shown using similar notation methods.

When light is described, for example, as blue incident light, the light may also be near-ultraviolet incident light. Similarly, when light is described as red incident light, the light may also be near-infrared incident light.

An embodiment configured by partially combining the aforementioned embodiments or the like also belongs to the present invention.

The present invention is not limited to the aforementioned embodiments, but various modifications or alterations can be made without departing from the spirit and scope of the present invention.

What is claimed is:

1. An endoscope apparatus comprising:
an image pickup device equipped with a color separation filter that color-separates and receives returning light of light radiated onto a subject by an illumination device to pick up an image of the subject;
an emphasis processing circuit that performs emphasis processing on sharpness of an image signal based on the image pickup device;
a storage device that stores information for modifying the processing contents of the emphasis processing circuit according to a type of the image pickup device and spectral characteristics of the returning light incident on the image pickup device which differ depending on whether a first observation mode in which image pickup is performed under illumination of white light or a second observation mode in which image pickup is performed under narrow band illumination light;
in the second observation mode, a first matrix circuit that performs matrix calculation for generating color signals of G and B from an image signal based on the image pickup device, and a signal intensity ration calculation circuit that dynamically calculates a signal intensity ration between the G and B color signals based on changes according to the returning light from the subject in field or frame units in a state where a coefficient of the matrix calculation performed by the first matrix circuit is set according to the type of the image pickup device; and
a control circuit that performs control of modifying the processing contents of the emphasis processing circuit based on the information of the storage device,
wherein the storage section stores, when the observation mode is the first observation mode, first information for setting an image signal to be subjected to emphasis processing by the emphasis processing circuit to a luminance signal and two color difference signals, and stores, when the observation mode is the second observation mode, second information for setting an image signal to be subjected to emphasis processing by the emphasis processing circuit to a luminance signal and one color difference signal, the first and second information being stored as the information for modifying processing contents of the emphasis processing circuit,
in the first observation mode and the second observation mode, the emphasis processing circuit performs emphasis processing on the color difference signal in the image signal with a smaller emphasis characteristic than on the luminance signal in the image signal in a frequency domain on a high frequency side having a higher frequency, and
only in the second observation mode, the control circuit performs control to generate the luminance signal which reflects the signal intensity ration dynamically calculated by the signal intensity ration calculation circuit as the luminance signal in the second observation mode.

2. The endoscope apparatus according to claim 1, wherein the storage device stores the first information and second information for performing emphasis processing on the luminance signal and the one color difference signal or the two color difference signals in the image signal inputted to the emphasis processing circuit using the different emphasis characteristics according to an array structure corresponding to unit pixels of a plurality of filter elements making up the color separation filter and having different transmission characteristics.

3. The endoscope apparatus according to claim 1, wherein the emphasis processing circuit performs emphasis processing on a specific color difference signal in the image signal with the smaller emphasis characteristic than on the luminance signal in the image signal in a frequency domain on a high frequency side having a higher frequency.

4. The endoscope apparatus according to claim 1, wherein the image pickup device is any one of a single CCD image pickup device, a double CCD image pickup device and a triple CCD image pickup device.

5. The endoscope apparatus according to claim 1, wherein the image pickup device comprises a single CCD image pickup device and the color separation filter comprises a complementary color filter.

6. The endoscope apparatus according to claim 1, wherein in the second observation mode, the control circuit sets the signal intensity ratio between the G and B color signals dynamically calculated by the signal intensity ratio calculation circuit as t and u, and controls the matrix calculation so as to generate the luminance signal reflecting the signal intensity ratio between the G and B color signals by using matrix elements of 0, t and u with a signal intensity ratio of a color signal of R being 0.

7. The endoscope apparatus according to claim 1, further comprising a second matrix circuit for generating second color signals of R, G and B reflecting the signal intensity ratio from the luminance signal reflecting the signal intensity ratio dynamically calculated by the signal intensity ratio calculation circuit and two color difference signals.

* * * * *